US011974937B2

(12) United States Patent
Glasroe

(10) Patent No.: US 11,974,937 B2
(45) Date of Patent: May 7, 2024

(54) INCONTINENCE ASSISTANCE APPLIANCES AND GARMENTS

(71) Applicant: Chiara Carolyn Glasroe, Brisbane (AU)

(72) Inventor: Chiara Carolyn Glasroe, Brisbane (AU)

(73) Assignee: Dignify Holdings Pty. Ltd. (AU)

(*) Notice: Subject to any disclaimer, the term of this patent is extended or adjusted under 35 U.S.C. 154(b) by 114 days.

(21) Appl. No.: 16/771,929

(22) PCT Filed: Dec. 12, 2018

(86) PCT No.: PCT/AU2018/051327
§ 371 (c)(1),
(2) Date: Jun. 11, 2020

(87) PCT Pub. No.: WO2019/113641
PCT Pub. Date: Jun. 20, 2019

(65) Prior Publication Data
US 2020/0405521 A1 Dec. 31, 2020

(30) Foreign Application Priority Data
Dec. 15, 2017 (AU) .................... 2017905026

(51) Int. Cl.
*A61F 5/44* (2006.01)
*A61F 5/48* (2006.01)
(Continued)

(52) U.S. Cl.
CPC .......... *A61F 5/4401* (2013.01); *A61F 5/4408* (2013.01); *A61F 5/485* (2013.01);
(Continued)

(58) Field of Classification Search
CPC ...... A61F 5/4401; A61F 5/4408; A61F 5/485; A61F 13/42; A61F 2013/422;
(Continued)

(56) References Cited

U.S. PATENT DOCUMENTS 3,890,973 A * 6/1975 Davis .................. A61F 13/495
604/355
4,695,279 A 9/1987 Steer
(Continued)

FOREIGN PATENT DOCUMENTS

CN 105919713 A 9/2016
DE 202005008071 U1 * 7/2005 ................ A61J 1/10
(Continued)

OTHER PUBLICATIONS

Grundke, Mobile Urine Drainage Bag With Holder, For Connection To Catheter Or Sheath In Cases Of Urinary Incontinence, Contains Superabsorber In At Least One Chamber Formed By Interconnected Sections, Jul. 21, 2005, PGPUB Translation (Year: 2005).*
(Continued)

*Primary Examiner* — Nicholas J. Weiss
*Assistant Examiner* — Brandon W. Levy
(74) *Attorney, Agent, or Firm* — Womble Bond Dickinson (US) LLP

(57) ABSTRACT

An incontinence assist appliance for a user includes an envelope including a surface, such as an upper outside surface, for contact with the user. A removable bladder is receivable within the envelope and includes a port for attachment of a catheter which passes through an opening in the outer envelope. The bladder contains a urine absorbing substance so that it avoids spills of liquid urine. The envelope may be formed as a wearable garment. A pair of trousers incorporating the appliance in each leg is also provided.

26 Claims, 18 Drawing Sheets

(51) Int. Cl.
  *A61F 13/42* (2006.01)
  *A61M 25/00* (2006.01)
  *A61M 39/12* (2006.01)
(52) U.S. Cl.
  CPC ......... *A61F 13/42* (2013.01); *A61M 25/0017* (2013.01); *A61M 39/12* (2013.01); *A61F 2013/422* (2013.01); *A61F 2013/427* (2013.01); *A61M 2202/0496* (2013.01)
(58) Field of Classification Search
  CPC .................. A61F 2013/427; A61F 5/48; A61F 2005/4402; A61F 5/451; A61F 13/537; A61F 2013/530481; A61F 13/5323; A61F 13/49007; A61F 5/44; A61F 13/66–82; A61F 13/00068; A61F 2013/00174; A61F 2013/00536; A61F 2013/00519; A61F 2013/0054; A61F 13/00063; A61F 13/069; A61F 13/0203; A61F 2013/00868; A61F 2013/00561; A61F 2013/00255; A61F 2013/00863; A61F 2013/00634; A61F 13/0206; A61F 13/0216; A61F 5/453; A61F 5/455; A61F 13/0223; A61F 13/5376; A61F 13/15203; A61F 13/49003; A61F 13/49; A61F 13/495; A61M 25/0017; A61M 39/12; A61M 2202/0496; A61M 1/915; A61L 15/60; A61L 15/24; A61L 28/0015; C08L 33/02
  See application file for complete search history.

(56) References Cited

U.S. PATENT DOCUMENTS

| | | | |
|---|---|---|---|
| 4,820,291 A | 4/1989 | Terauchi et al. | |
| 5,387,201 A * | 2/1995 | Fowler ................ | A61M 3/0279 604/290 |
| 8,187,238 B1 | 5/2012 | Dupree | |
| 9,737,433 B2 | 8/2017 | Joh | |
| 2001/0031954 A1 * | 10/2001 | Jordan .............. | A61F 13/51496 604/385.01 |
| 2003/0096899 A1 * | 5/2003 | Pearce ................. | B29C 44/583 524/474 |
| 2003/0199844 A1 * | 10/2003 | LaVon ................. | A61F 13/505 604/385.14 |
| 2004/0176731 A1 * | 9/2004 | Cheng ..................... | A61F 5/455 604/329 |
| 2005/0124947 A1 | 6/2005 | Fernfors | |
| 2006/0155260 A1 * | 7/2006 | Blott ................... | A61M 3/0216 604/543 |
| 2008/0262451 A1 | 10/2008 | Broden | |
| 2010/0114047 A1 * | 5/2010 | Song ....................... | A61F 13/42 604/361 |
| 2012/0016326 A1 * | 1/2012 | Brennan ................. | A61L 15/60 604/372 |
| 2013/0019382 A1 * | 1/2013 | Herman .................. | A41F 11/00 2/327 |
| 2015/0112228 A1 * | 4/2015 | Ekema .................. | A61F 5/4408 600/584 |
| 2015/0257948 A1 | 9/2015 | Steele | |
| 2017/0100276 A1 * | 4/2017 | Joh ........................ | A61F 5/453 |

FOREIGN PATENT DOCUMENTS

| | | | |
|---|---|---|---|
| DE | 202005008071 U1 | 7/2005 | |
| EP | 1068848 A1 * | 1/2001 | ............ A61F 5/451 |
| EP | 1068848 A1 | 1/2001 | |
| GB | 1161015 A | 8/1969 | |
| GB | 2295766 A | 6/1996 | |
| GB | 2351909 A | 1/2001 | |
| GB | 2413766 A | 11/2005 | |
| JP | 2004-147818 A | 5/2004 | |
| KR | 102081491 B1 * | 2/2020 | |
| WO | 91004714 A2 | 4/1991 | |
| WO | WO-9104714 A2 * | 4/1991 | ............ A61F 5/451 |
| WO | 2016022795 A1 | 2/2016 | |

OTHER PUBLICATIONS

Won, Diaper for Dementia Patient, Feb. 25, 2020, PGPUB Translation (Year: 2020).*

International Search Report dated Jan. 22, 2019 for International Application No. PCT/AU2018/051327 in 5 pages.

Written Opinion of the International Searching Authority dated Jan. 22, 2019 for International Application No. PCT/AU2018/051327 in 8 pages.

International Preliminary Report on Patentability dated Nov. 11, 2019 for International Application No. PCT/AU2018/051327 in 5 pages.

Supplementary European Search Report dated Sep. 24, 2021 for European Patent Application No. EP 18888498.

* cited by examiner

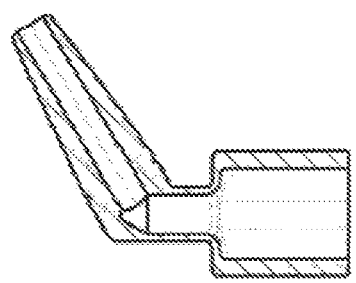
FIG. 10
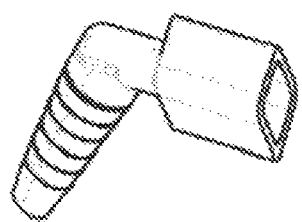
FIG. 11
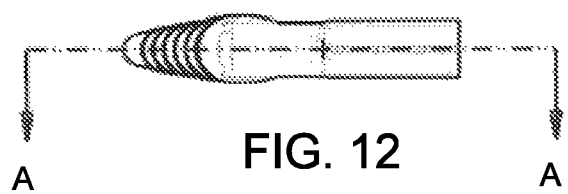
FIG. 12
 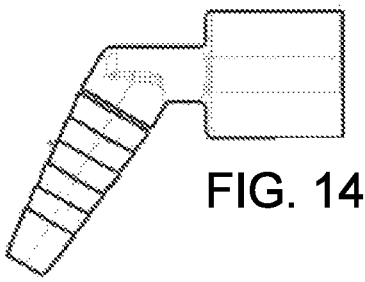 
FIG. 13  FIG. 14  FIG. 15
FIG. 16

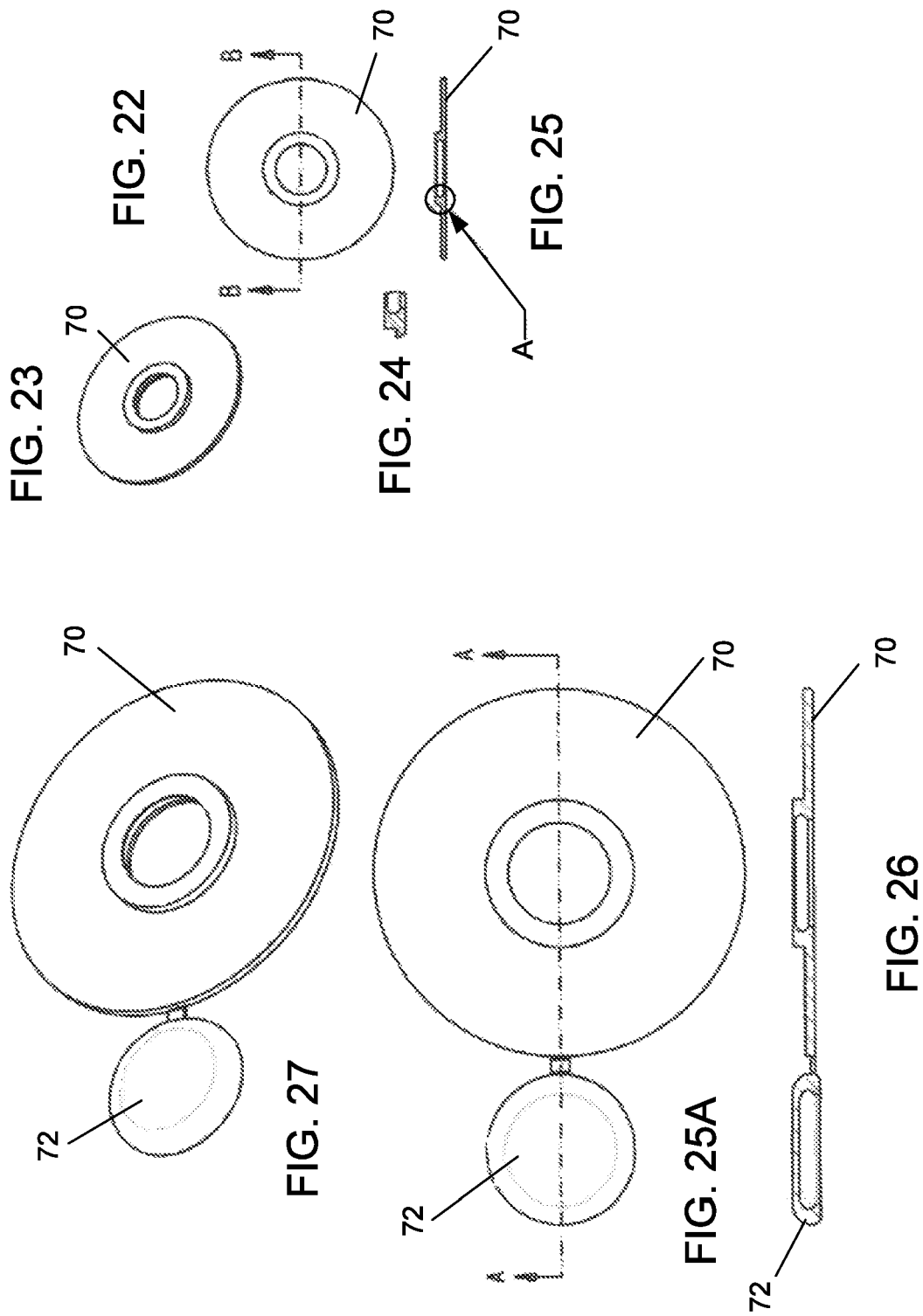

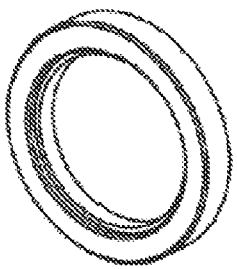
FIG. 28
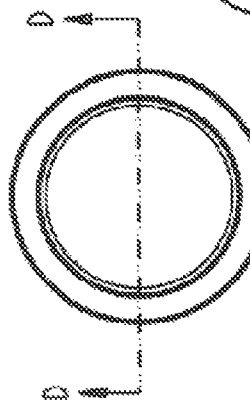
FIG. 29
FIG. 30
FIG. 31
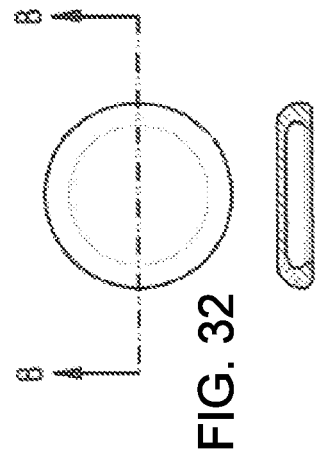
FIG. 32
FIG. 33
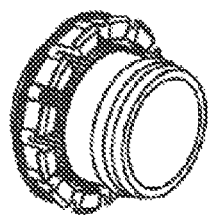
FIG. 34
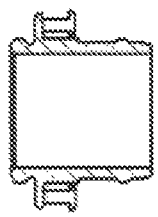
FIG. 37
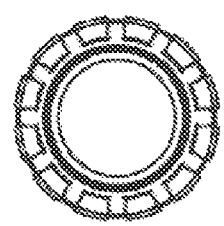
FIG. 35
FIG. 36
FIG. 38
FIG. 39
FIG. 40
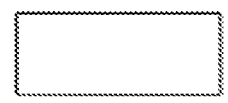
FIG. 41

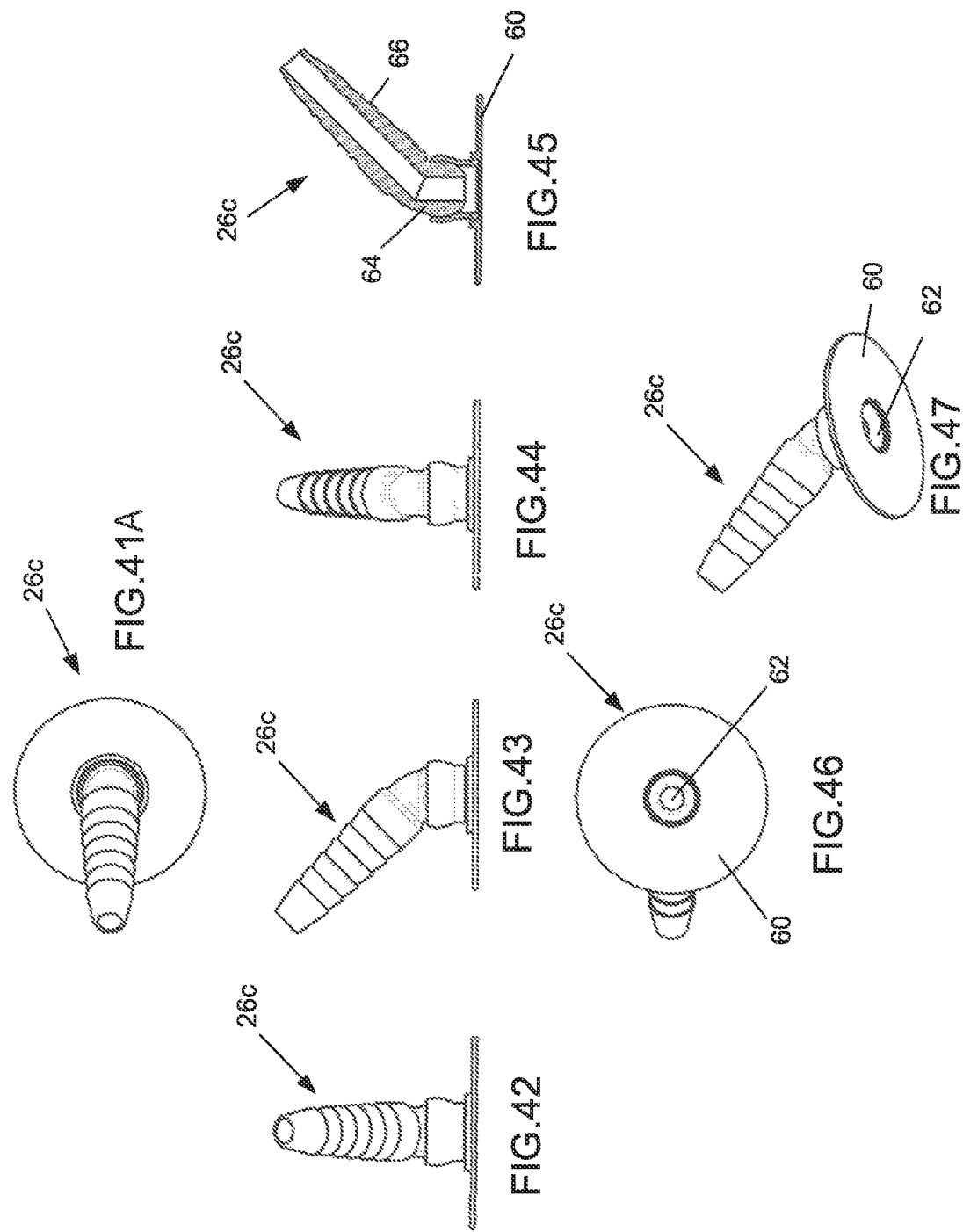

INCONTINENCE ASSISTANCE APPLIANCES AND GARMENTS

TECHNICAL FIELD

The present invention concerns an appliances and wearable garments that are used to assist in the placement of urinary catheters and in the control of incontinence.

BACKGROUND ART

Any references to methods, apparatus or documents of the prior art are not to be taken as constituting any evidence or admission that they formed, or form part of the common general knowledge.

The effective control of urinary discharges in facilities such as old age persons homes is an important factor in maintaining a hygienic and pleasant environment for carers and residents.

The need for such control has been exacerbated in recent years as the life expectancy of people has increased and with it the proportion of older people suffering from dementia. According to The National Centre for Social and Economic Modelling NATSEM (2016) Economic Cost of Dementia in Australia 2016-2056 there are more than 410,000 Australians living with Dementia. Unless there is a medical breakthrough the number of people with dementia is expected to reach over one million by 2056.

Dementia suffers can pose a particular problem in care facilities because they may exhibit a tendency to remove clothing, including diapers (or as they are sometimes called "pads") and to interfere with or remove urinary catheters. In doing so urinary bladders may be broken and urine leaked in onto the floor of the facility. Often urinary bladders are worn around the ankle so that a wearer may inadvertently knock and rupture the bladder. Cleaning up a urine spill and assisting residents in the replacement of catheters and clothing is a labor intensive and demanding activity that consumes the time of carers which could otherwise be much better spent. Such incidences may also reduce the quality of life for other residents.

Of course, people other than dementia suffers may need to be catheterized and/or have to deal with incontinence. For example, spinal injury patients may have such needs.

The present Inventor has spent much of her working life caring for residents of aged care and disabled facilities and has a strong appreciation of the need for such residents to be able to live their lives as comfortably as possible and with dignity.

It is an object of the present invention to provide an appliance for addressing the problems discussed above.

SUMMARY OF THE INVENTION

According to a first aspect of the present invention there is provided an incontinence assist appliance for a user comprising:
  an envelope including a surface for contact with the user; and
  a bladder that is removably receivable within the envelope, the bladder including a port for attachment of a catheter;
  wherein the bladder contains a urine absorbing substance.

In a preferred embodiment of the invention the urine absorbing substance comprises sodium polyacrylate.

Preferably the envelope is formed with an opening for the passage of a catheter from the bladder to the user.

The bladder may be provided with bladder status indicator which indicates when the bladder is full and needs to be changed.

The bladder status indicator preferably comprises a region of litmus dye.

The bladder may have a perimeter shaped to correspond to the envelope.

In a preferred embodiment of the invention the bladder is formed of a clear material.

The envelope may include an opening through which the bladder passes into an interior of the envelope for locating within the interior of the envelope in use.

Preferably the bladder status indicator is positioned in the bladder to locate adjacent the slit for ready inspection by a carer.

In a preferred embodiment of the invention the exterior of the bladder and the interior of the envelope are provided with complementary hook and loop fasteners (such as Velcro™) for detachably holding the bladder fast within the interior of the envelope.

In one embodiment the incontinence assist appliance further includes a pressure care layer. For example the pressure care layer may comprise a cushioning layer that locates above the envelope that contains the bladder.

For example, the cushioning layer may contain a polymer gel.

A detachable cover may be provided that fits over the pressure care layer and/or the envelope that contains the bladder.

Preferably the envelope in combination with the bladder presents as a cushion for seating of the user thereon. For example, the envelope in combination with the bladder may have a width by length of between 14"×16" and 18"×20" to suit wheelchairs and bed use.

The envelope may be formed as a wearable garment. For example, the envelope may be formed with lateral wings for placement around opposed sides of a waist of the user and a medially extending portion for bringing up between the user's legs wherein outer edges of the lateral wings fasten to a front portion extending from the medially extending portion in use. For example the envelope may include hook and loop fastening regions, such as Velcro® for attaching the outer edges of the lateral wings to the medially extending portion in use.

In a preferred embodiment of the invention the envelope further includes a security flap of sufficient length to extend from an attachment point over the fastening of the lateral wings with the medially extending portion to a rearward portion of the envelope in use that is inaccessible to a user to thereby make it difficult for the user to remove the envelope. Preferably a leading edge of the security flap and the rearward portion of the envelope include complementary fasteners.

Preferably the envelope includes at least one strap which extends from one of the lateral wings across the medially extending portion to the opposed lateral wings. In a preferred embodiment of the invention the at least one strap comprises a number of straps that extend from the opposed lateral wings to the medially extending portion.

Preferably the medially extending portion is formed with loops for passage of the one or more straps therethrough.

The medially extending portion may have a distal end that is formed with an opening for bladder installation. Preferably a further opening for bladder installation is provided through a rear portion of an external layer of the envelope.

A pair of short trousers including first and second leg portions wherein each leg portion comprises the previously described incontinence assist appliance.

Preferably the short trousers are formed with inner loops which retain catheter tubes for connection to the bladders of the incontinence assist appliances.

In a preferred embodiment of the invention the short trousers have a waist that is adapted for suspenders to be fitted thereto.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIGS. 10 to 16 are various views of a fixed bladder connector shown in use in FIG. 9.

FIGS. 22 to 25 are details of a plate of the connector of FIGS. 17-21 which locates inside the bladder.

FIGS. 25A to 27 are plan, cross-sectional and perspective views of the plate in combination with a seal for sealing the connector subsequent to removal of the catheter shown as moulded in a single piece.

FIGS. 28 to 38 are views of components of the pants' bladder connector of FIGS. 17 to 21.

FIGS. 39 to 41 are perspective, end and side views of a portion of catheter tube.

FIGS. 41A to 47 are views of a swiveling connector which may be used with the bladder of the incontinence applicance of FIGS. 1 to 2C FIGS. 48 to 54 are views of a swivelling connector which may be used, for example, with the of the short trousers garment of FIG. 6.

DETAILED DESCRIPTION OF PREFERRED EMBODIMENTS

In the following description a number of exemplary embodiments of the invention will be discussed. Throughout the discussion like components and features will be identified from embodiment to embodiment with the same identifier numerals in the figures.

Figure 1:
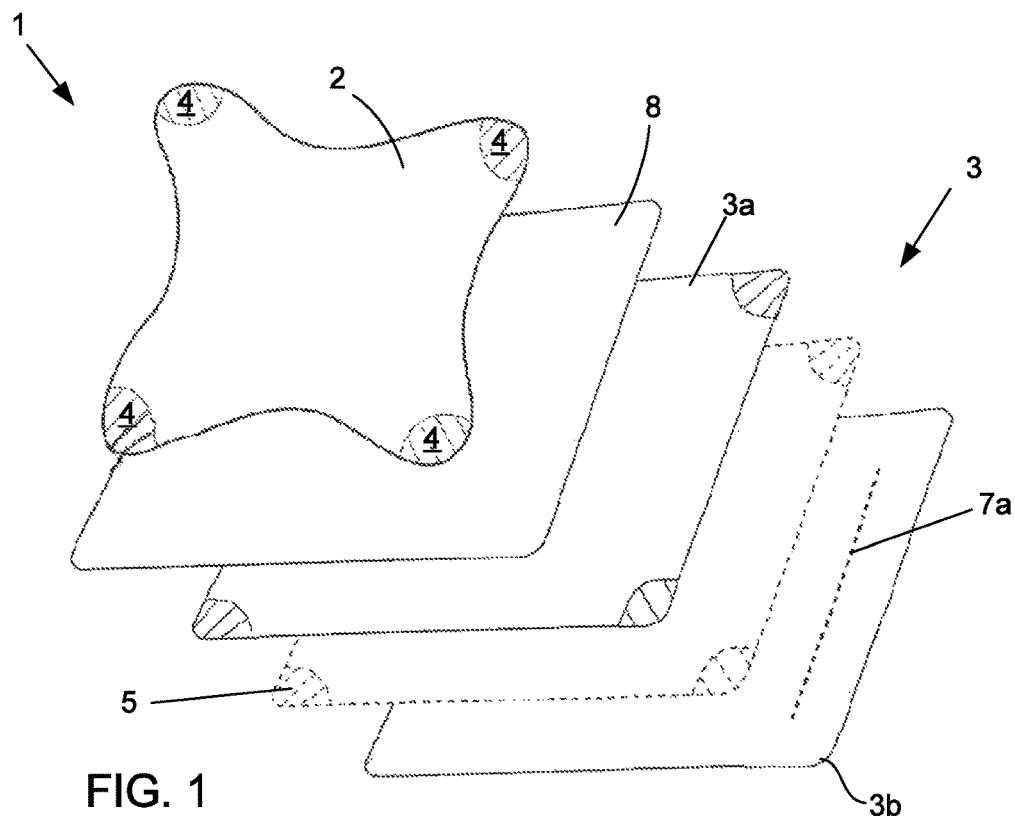
FIG. 1 illustrate layers comprising an incontinence assist appliance in the form of a cushion, according to a first embodiment of the present invention.
Figure 2A:
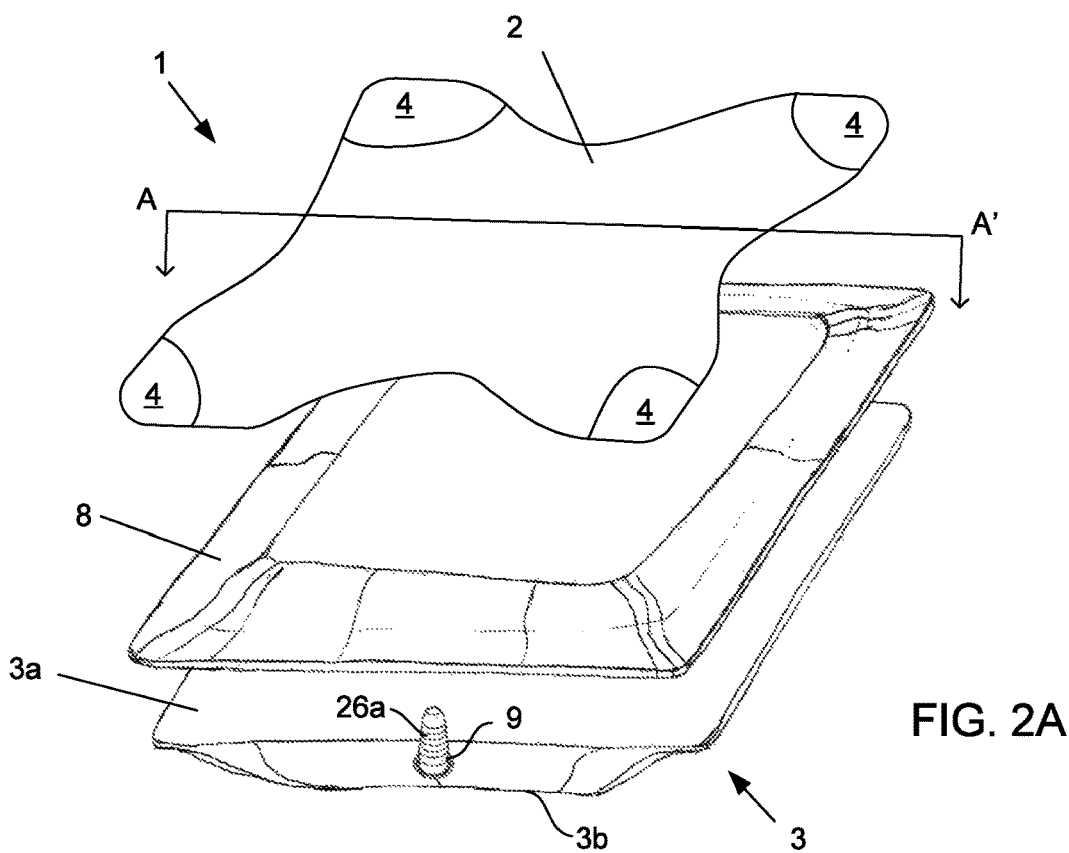
FIG. 2A Is a partially exploded perspective view of the cushion of FIG. 1.
Figure 2B:
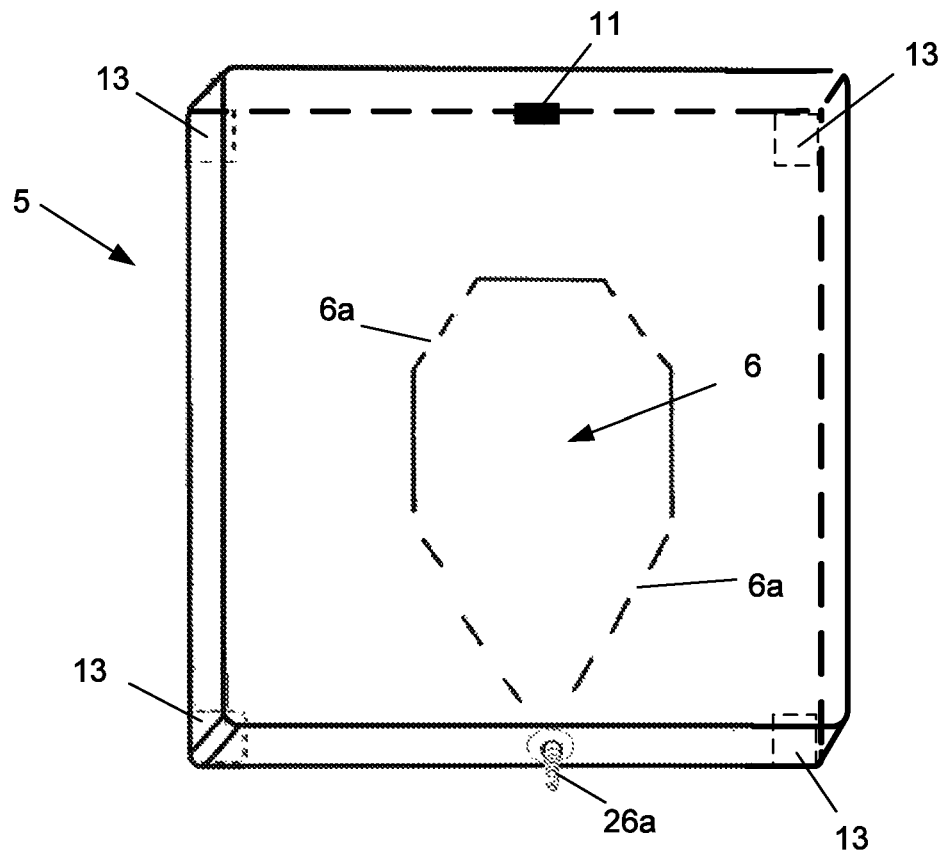
FIG. 2B is a perspective view of a bladder of the incontinence assist appliance of FIG. 1

Referring now to FIG. 1, a diagram is provided showing a number of layers which comprise an incontinence assist appliance 1 for a user according to a first embodiment of the invention. FIG. 2A is a perspective, and somewhat exploded view of the incontinence assist appliance 1 in use with cover 2 detached from permanent gel cushioning layer 8. The appliance 1 comprises an envelope 3 including a top layer 3a and a bottom layer 3b which are fastened together around their edges and between which a removable bladder 5 is placed. The top layer 3a is suitable for contact with the user or a cushion may be placed over the top layer 3a as will be described. As mentioned, the envelope 3 contains the removable bladder 5, which is shown in FIG. 2B and which is receivable within the envelope 3 through an opening in the form of a slit 7a formed through bottom layer 3b of the envelope 3. Preferably the opening is a "pillow slip" style opening so that a flap (not shown) is provided which covers the opening in normal use. The bladder 5 contains a urine absorbing substance such as sodium polyacrylate.

A manifold 6 which comprises a plastic sack is located within the bladder 5 and is surrounded by the sodium polyacrylate of the bladder. A tubular connector 26a is fastened to the bladder and is in fluid communication with an inlet to the manifold 6. The manifold 6 is formed with a number of exit holes 6a therethrough for distributing urine entering the sack 6 from tubular connector 26a to the surrounding sodium polyacrylate in order to assist in uniformly distributing the urine throughout the sodium polyacrylate to reduce the likelihood of wet spots developing in use.

The envelope 3 is formed with an opening 9 through which the tubular connector 26a passes. In use the tubular connector 26a is connected to a catheter which is applied to a user. Urine passes through the catheter in use, through the tubular connector 26 into the manifold 6, out of the manifold through the exit holes 6a and thence into the sodium polyacrylate of the bladder 5. FIGS. 41A to 47 comprise various views of connector 26a. The connector 26a includes a base plate 60 which locates within the bladder 5 and which includes a central opening 62 for passage of urine therethrough. A hollow socket 64 extends about the central opening from the baseplate and receives a bulbous end of an externally barbed tube 66 about which a catheter locates in use. Accordingly the connector tube 66, which is angled, may be swiveled relative to the base plate 5 to assume a desired angle.

With reference again to FIG. 2B, the bladder 5 is provided with a bladder status indicator in the form of a region of litmus dye 11, which indicates when the bladder is full and needs to be changed.

The region of litmus dye 11 is positioned in the bladder 5, which has transparent walls, so that it locates adjacent the slit 7a through the bottom layer 3b in order that it can be seen through the slit 7a for ready inspection by a carer.

The bladder 5 has a perimeter, which in the present embodiment is a rectangle but which in other embodiments may be another shape that corresponds to the interior of the envelope 3.

The exterior of the bladder 5 and the interior of the envelope 3 are provided with complementary hook and loop fasteners 13 (such as Velcro®) for detachably holding the bladder 5 fast within the interior of the envelope 3.

The appliance 1, comprising the envelope 3 in combination with the bladder 5 presents as a cushion for seating of the user thereon. For example, the envelope in combination with the bladder may have a width by length of between 14"×16" and 18"×20" to suit wheelchairs and bed use.

Referring again to FIG. 1, the outer topside of the envelope 3 may be located beneath a cushioning layer 8 (as shown in the schematic cross sectional diagram of FIG. 2C which shows the layers in cross section along the line A-A' of FIG. 2A) that includes cushioning material such as polymer gel. FIG. 2A shows, in somewhat exploded view, the envelope 3, which contains the bladder 5 and from which connector 26a extends, and the top layer 8 of cushioning material located above it which contains the polymer gel.

Figure 2C:
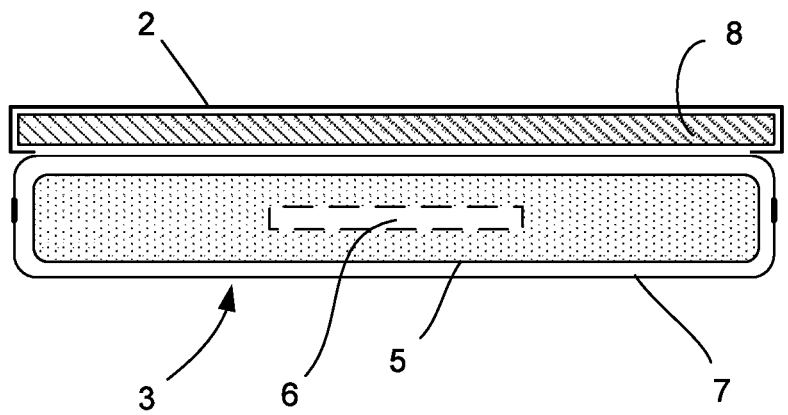
FIG. 2C is a cross sectional view through an incontinence assist appliance similar to that of FIG. 2A showing an upper cushioning layer with cover thereover and a lower layer comprising an envelope that contains an internal urine absorption layer in the form of the bladder of FIG. 2B.

As shown in FIGS. 1, 2A and 2C a top cover 2 may be provided with corner pockets 4. The top cover 2 locates over the top layer 8 with its sides coming down and with the pockets 4 fastening under the corners of the top layer 8 to keep the top cover 2 in place over cushion layer 8. The top cover 2 assists in keeping the top layer 8 from becoming hot, irritating or unsuitable to a user's skin.

The embodiment of the invention that has been described with reference to FIGS. 1 to 2C is suitable for community activities, home environment and hospitals, including intensive care units (ICUs). It is useful for infants and elderly nursing homes, hostels, youth and disability housing. It may also be suitable for veterinary surgeries, animal shelters, wildlife centres and zoos Furthermore, the embodiment of the invention that has been described with reference to FIGS. 1 to 2C is believed to have a number of benefits as follows:

- Catheter cushion remains secure under clients in bed/wheel chair
- No drainage bag hanging from bed rail or dragging on the floor
- No undergarment or clothing required eg; ICU in hospital
- Pressure cushion replaces current expensive non-recyclable pads
- Pressure cushion can be sprayed for cleaning and is reusable
- Both males and females can use the pressure cushion design
- Velcro holds the bladder secure to the pressure cushion
- Solving clients objectives e.g.; ideally for non-ambulant clients
- Animal recovery including repositioning on pressure cushion
- Opening for the bladder is absent from clients sight
- Short tube to catheter preventing kinking or recurrent blockages
- Minimising or avoiding health complications eg; UTI's urinary tract infections
- Packs of one and two for short term and long term catheter usage
- Different sizes to fit wheel chairs and different size pressure pads
- Permanent top layer of gel to prevent bed sores
- Bladder may be weighed for measuring/monitoring volume levels
- Bladder connector may be capped for movement with fitting on bladder (one type).
- Bladder is not flush or adjacent to the skin
- Bladder connects flat and attached internally with velcro for stability
- Litmus dye indicates when bladder needs replacing by changing colour
- Bladder contains sodium polyacrylate that turns urine into gel and prevents leakage
- Three litres of urine is one full day's maximum volume capacity
- Bladder and inner compartment are clear to sight any possible blood in urine
- Packs of ten or carton disposable bladders for replacements
- The cover 2 prevents gel 8 being flush or adjacent to skin and is easily connected to the appliance and is removable for cleaning.

Figure 3A:
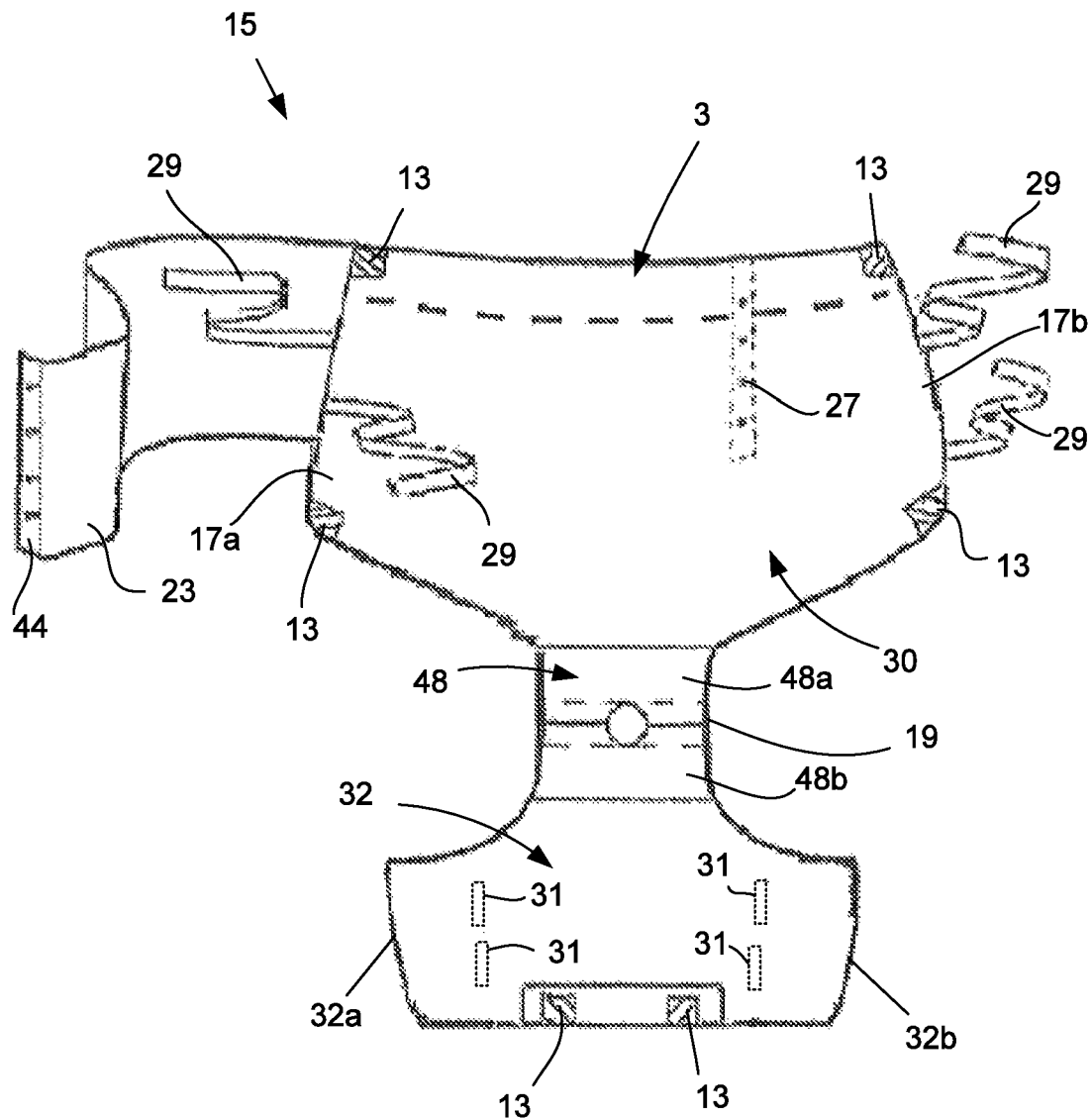
FIG. 3A illustrates a wearable incontinence assist appliance comprising a pair of pants, shown in an unfurled configuration, according to a second embodiment of the present invention.
Figure 3B:
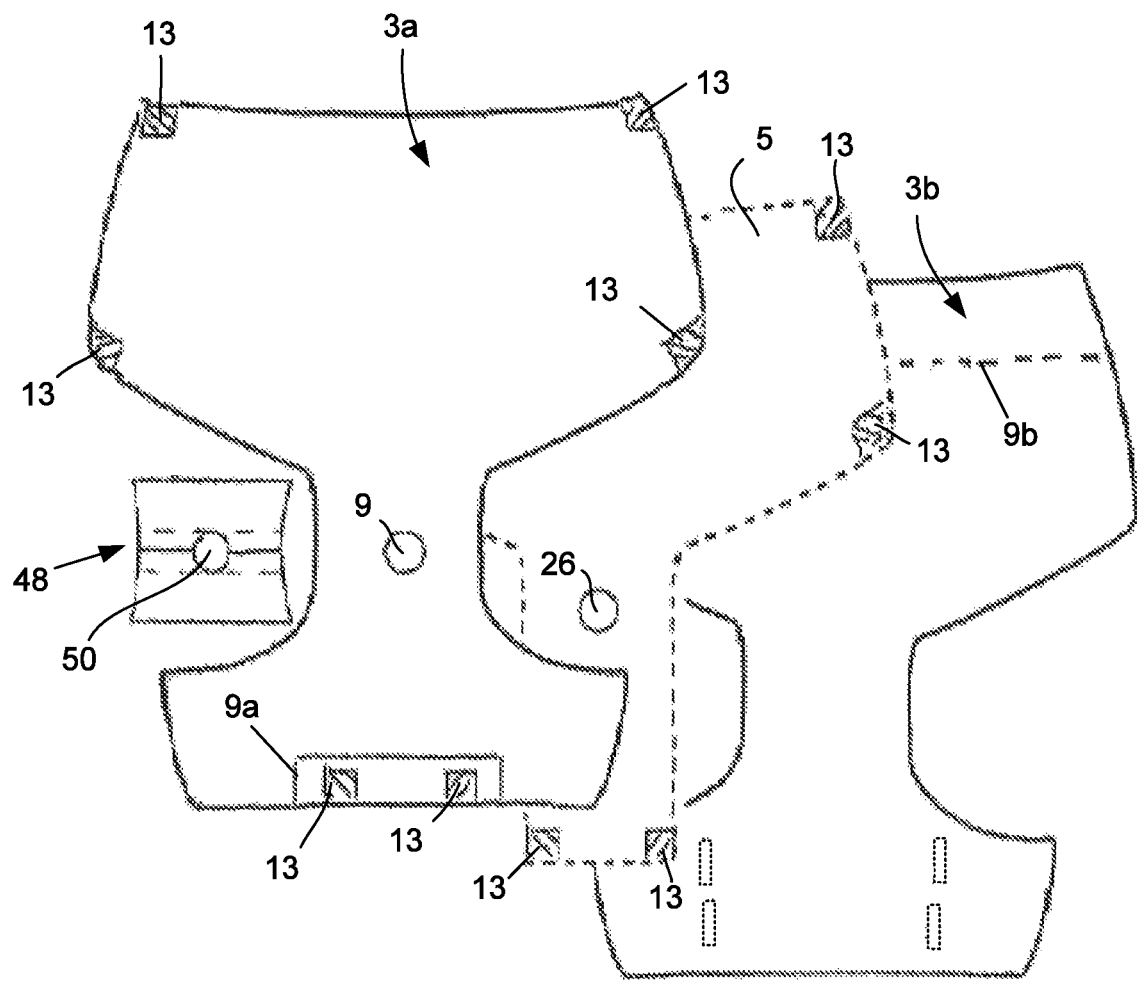
FIG. 3B is a diagram showing various layers of the pants of FIG. 3A.
Figure 3C:
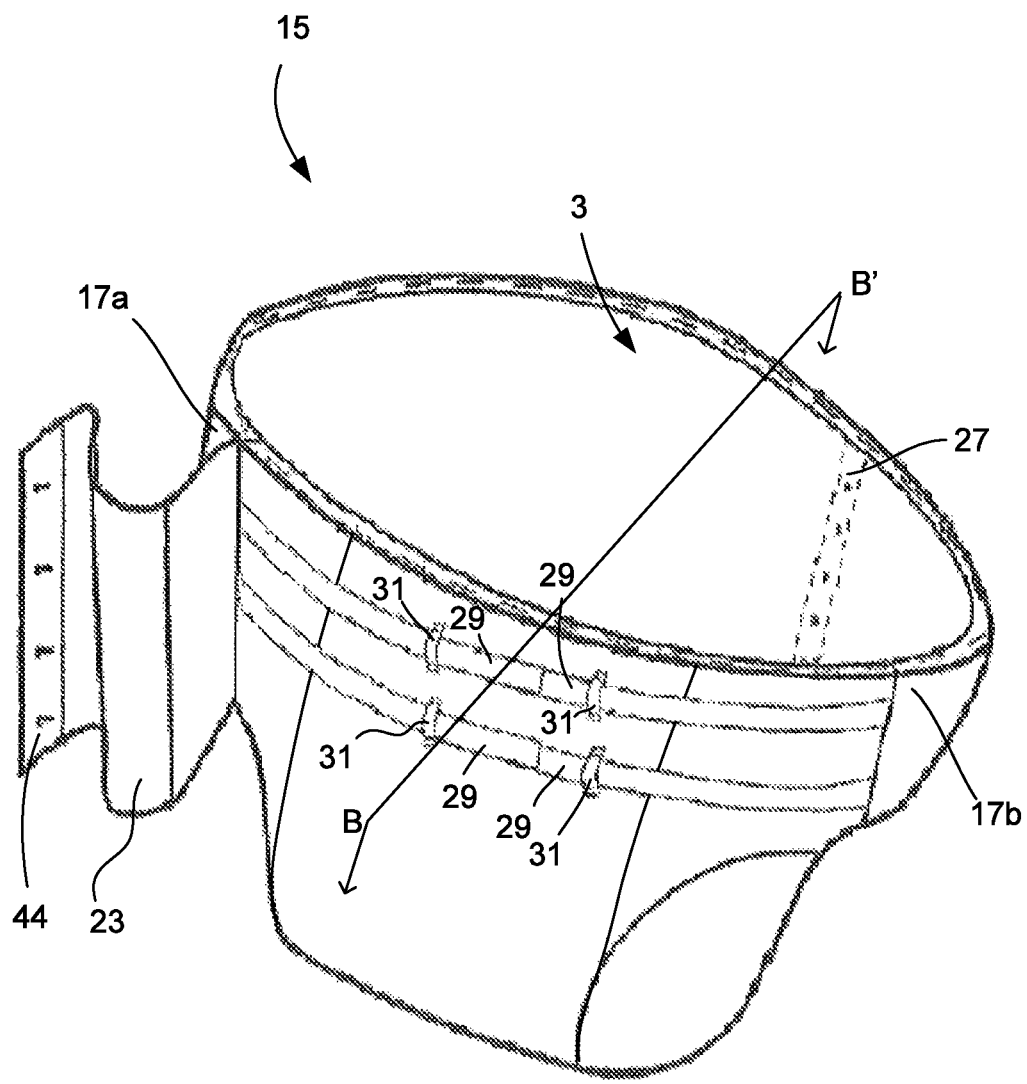
FIG. 3C shows the pants as worn by a user prior to fastening of securing flap 23.

The envelope 3 may be formed as a wearable garment for example a pair of pants 15, the inner side of which is illustrated in an unfurled configuration in FIG. 3A. FIG. 3B is an exploded view of garment 3A showing that the envelope 3 is comprised of an internal layer 3a, which makes contact with a wearer in use, and an external layer 3b. The internal layer 3a and the external layer 3b are sewn or otherwise fastened together around their peripheries and house a bladder 5 which will be subsequently discussed with reference to FIG. 4. Pillow slip openings 9a and 9b are provided in the internal layer 3a and the external layer 3b to assist a carer in inserting and replacing the bladder 5 within the envelope 3. FIG. 3C shows the pants 15 in the assembled state in which they would be worn just prior to fastening security flap 23. The relative positioning of the various layers can be further discerned in the cross sectional view of FIG. 5.

Returning again to FIG. 3A, the envelope 3 is formed with a back portion 30 and a front portion 32 that are interconnected by a rectangular, medial gusset portion 19. The back portion 30 includes lateral wings 17a, 17b for placement around opposed sides of a waist of the user wherein the medially extending gusset portion 19 locates between the user's legs with the front panel 32 extending upwardly. The outer edges of the lateral wings 17a, 17b are brought adjacent to, or overlapping of, the lateral edges 32a, 32b of the front portion 32 in use.

The envelope 3 of pants 15 further includes a security flap 23 which has a leading vertical edge 44 down which a number of security flap fasteners 46 are located. The security flap 23 is of sufficient length to extend from lateral edge 17a of rear portion 30 and over the front portion 32 to complementary rear fasteners 27 to which the security flap fasteners 44 attach. Since the security flap 23 wraps around to the rear where it fastens, it is difficult for a user to access the fasteners and thus is difficult for the user to remove the envelope 3, which is advantageous where the user suffers from dementia for example and might otherwise inappropriately remove the pants.

The pants 15 include straps 29 that bear complementary Velcro™ ends and which extend from opposed sides of the lateral wings 17a, 17b to fasten across the front portion 32 where they are covered by the security flap 23.

As can be seen in FIG. 3C, the front portion 32 is formed with loops 31 for passage of the straps 29 therethrough in order to retain them in place.

Figure 4:
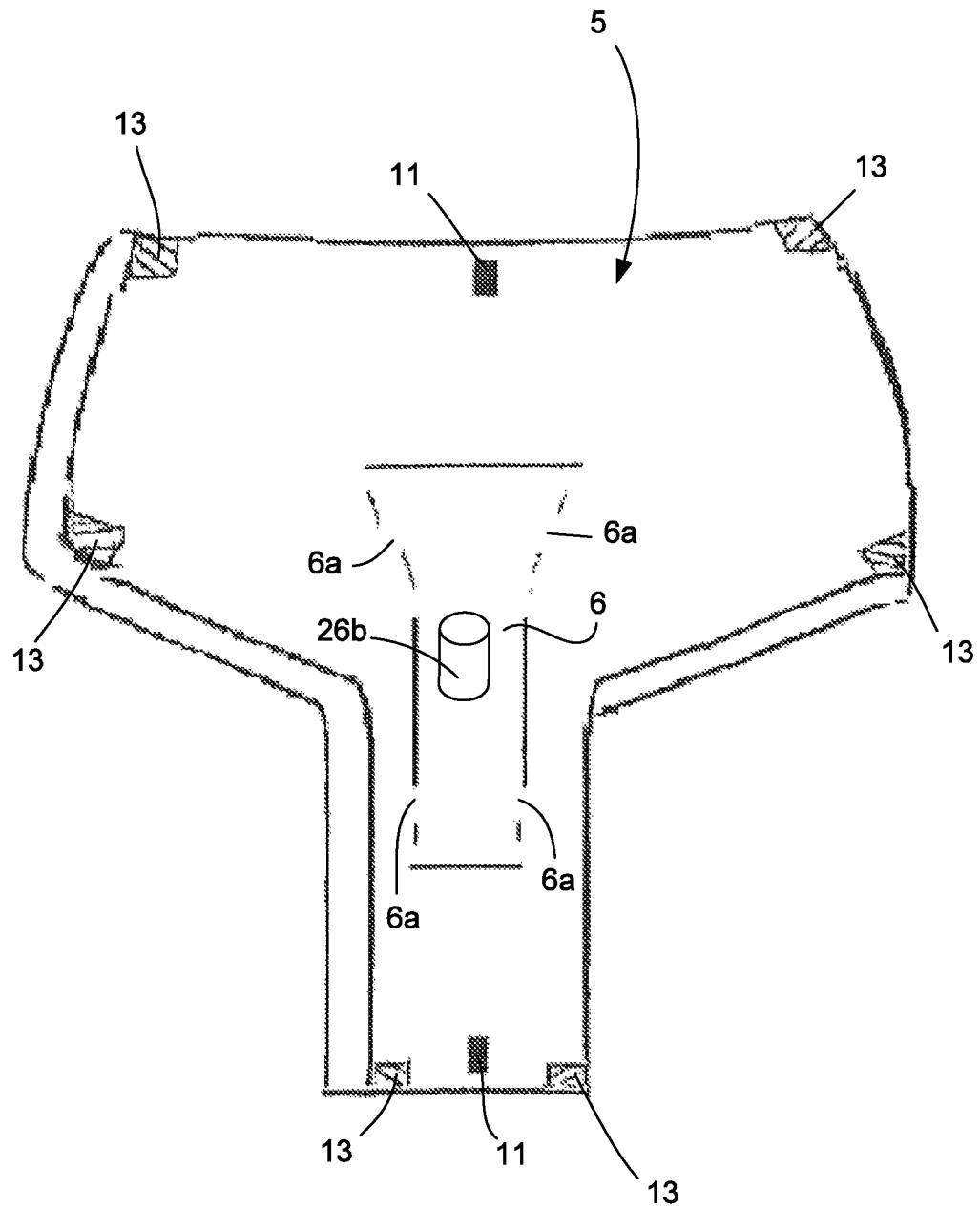
FIG. 4 is a perspective view of a bladder of the pants of FIG. 3A.

FIG. 4 is a view of the bladder 5 for the garment 15 showing the placement of Velcro™ patches 13, litmus indicator 11 and internal manifold 6 with tubular connector 26b attached thereto for connection of a urine catheter. FIGS. 17 to 21 shown connector 26b coupled to a catheter tube 68. FIGS. 22 to 25 show a base plate 70 of connector 26B which locates within the bladder 5. FIGS. 25A to 27 show the base plate 70 as molded together with a cap 72 which can be used to seal the connector 26b upon removing the catheter tube 68. Consequently there is no need to remove the catheter from the user in order to remove the pants 15 since the connector 26b can be readily sealed with cap 72. FIGS. 28 to 38 comprise various views of components of connector 26B.

The urine bladder includes litmus dye indicator regions 11 as previously discussed in relation to the bladder of FIG. 2 to assist a carer in determining when the bladder 5 needs to be replaced.

The pants 15 contain urine bladder 5, shown in FIG. 4 that is shaped to correspond to the shape of the envelope 3. The urine bladder 5 includes an internal manifold 6 comprising a plastic sack with perforations 6a for distributing urine to the urine absorbing material in the form of sodium polyacrylate within the bladder. The bladder 5 includes a catheter port comprising the tubular connector 26b that is coupled to the manifold 6 and which is for connection to catheter tube 68 that passes through a hole 9 in the internal layer 3a of the envelope 3 to the user. FIGS. 39 to 41 illustrate a short length of the catheter tube 68. The bladder 5 is fastened to the inside of the inner layer 3a by means of the complementary hook and loop (e.g. Velcro™) fasteners 13 which have corresponding parts that are attached to the bladder and to the inner side of the internal layer 3a.

Figure 5:
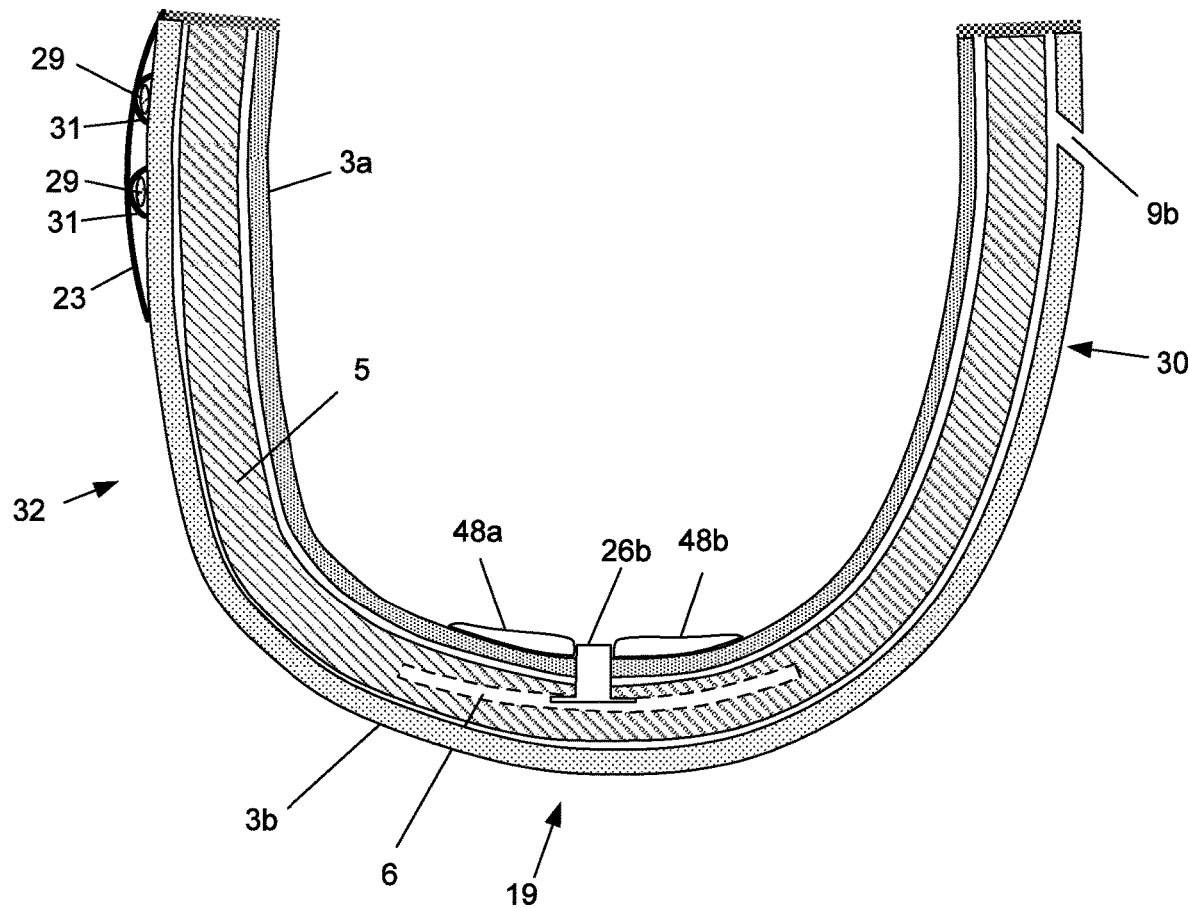
FIG. 5 is a cross sectional view through the pants of FIG. 3C along the line B-B', with the security flap 23 fastened in place.
Figure 5A:
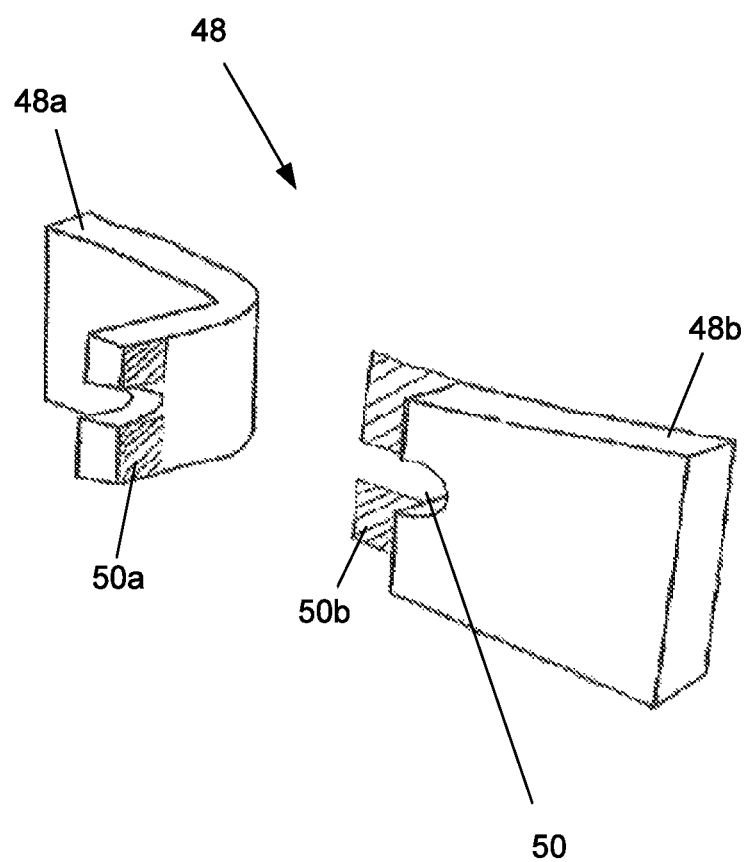
FIG. 5A is a dissembled view of a two part gel cushion of the pants of FIG. 3A.

As can be seen in FIGS. 3A, 3B and 5 a gel cushioning pad 48 is provided with a hole 50 therethough that corresponds to the hole 9 through the inner layer 3a and which is positioned over the tubular connector 26b for cushioning the user. As shown in FIG. 5A, the gel pad 48 is formed in two parts 48a and 48b with hook and loop portions 50a and 50b affixed to each for fastening the two parts 48a and 48b together to allow for placement of a balloon port and connection underneath.

Figure 6:
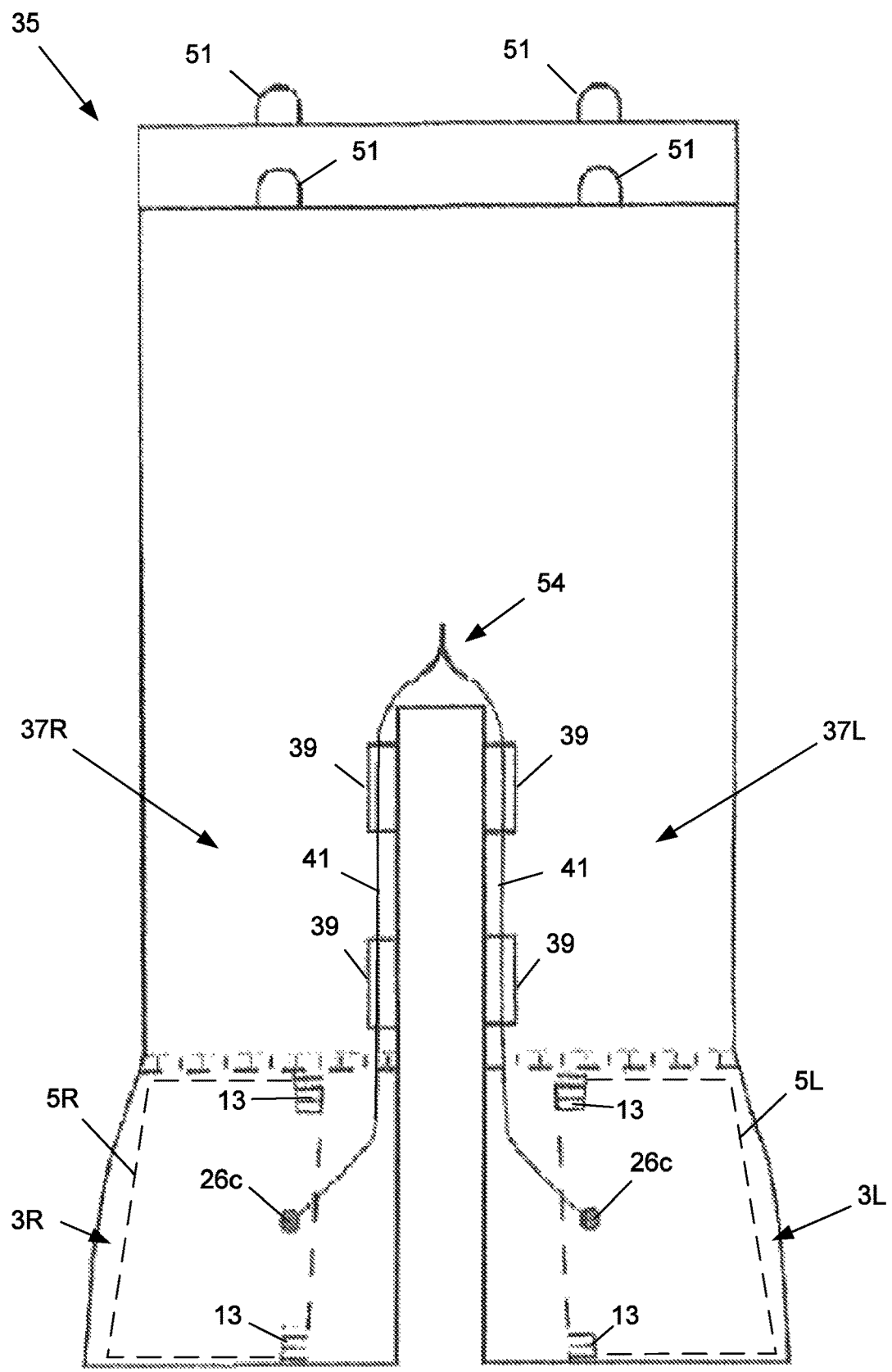
FIG. 6 shows a wearable garment being a pair of short trousers according to a third embodiment of the present invention.
Figure 7:
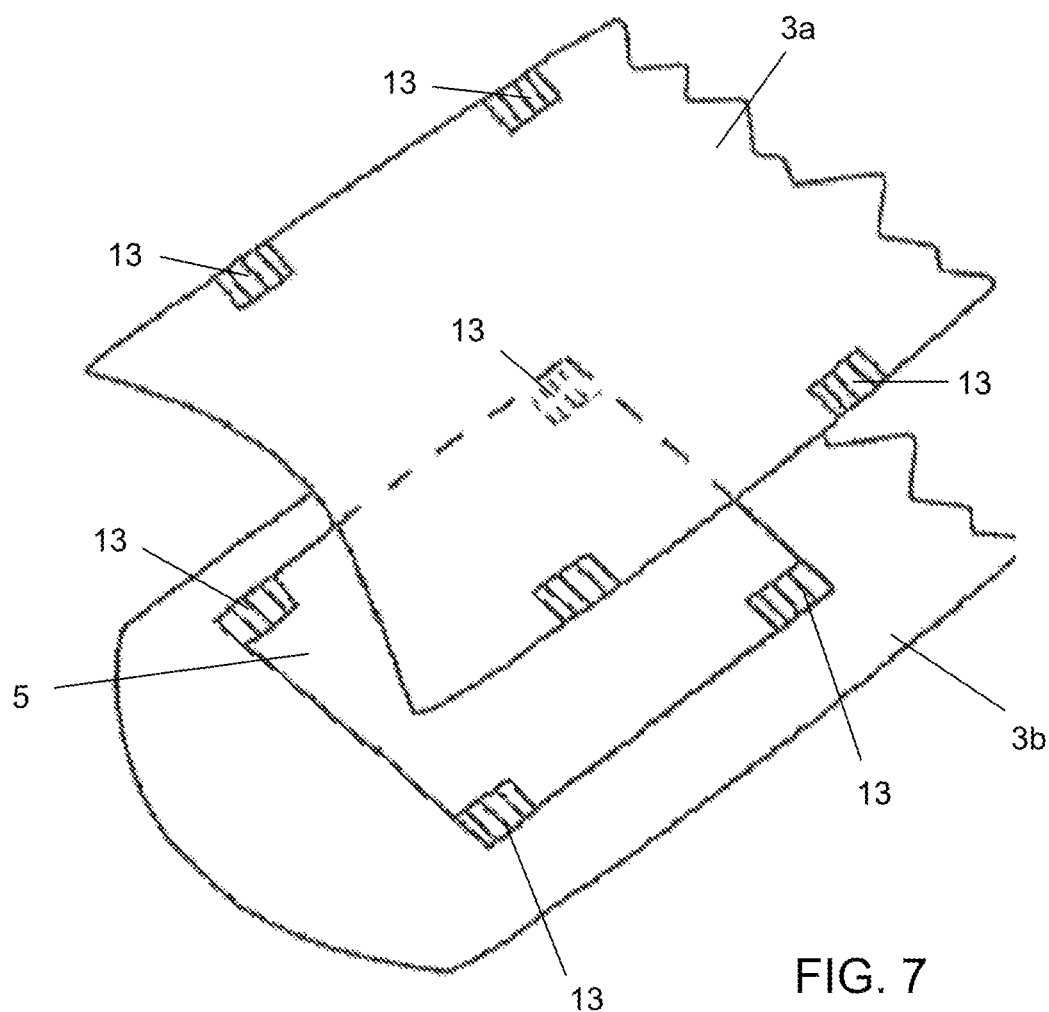
FIG. 7 is an exploded view of a portion of a lower leg of the garment comprising an envelope comprised of an internal layer of material and an external layer of material with a bladder located therebetween.
Figure 8:
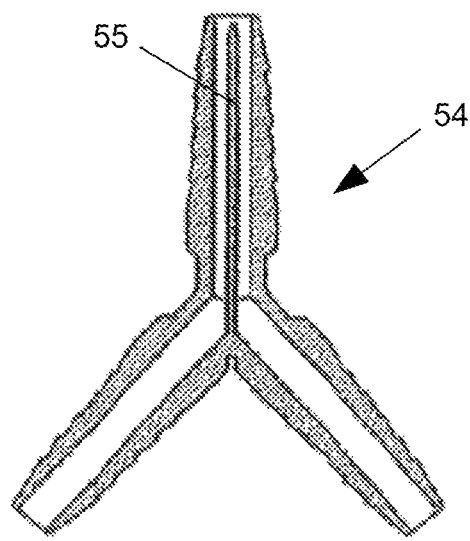
FIG. 8 is a cross sectional view through a "y" shaped connector for connecting a urine catheter simultaneously to left and right tubes coupled to left and right lower leg bladders of the garment of FIG. 6.

The embodiment of the invention that has been discussed with reference to FIGS. 3 to 5A is suitable for community activities, home environment and hospital rehabilitation. It is also appropriate for nursing homes, hostels, youth and disability housing There are believed to be numerous benefits of the embodiment of the invention in the form of the pants that have been described with reference to FIGS. 3 to 5A as follows:

Pants remain immovable and secure for clients dignity
No drainage bag attached to one leg/bedrail or dragging on the floor
Prevents the additional risk of the client/carer pulling out the catheter
Comfortable wearing with no leakage of urine or feces on the floor etc
Velcro hooks through the front flap to hold pants and bladder secure
Pants replace current expensive non-recyclable pads
Current pads can be covered with Pants design for immovable (without catheter)
Security flap fastens around the front to the back 180 degrees thereby preventing client constantly releasing and removing the pants.
Solving clients objectives eg; ideally for dementia clients with/without catheter for dignity.
Double cotton jersey pants is washable and reusable
Both males and females can wear the pants design
Pillow slip type openings assists the installation of the bladder in this confined area
Opening for the bladder insert is absent from clients sight
Different packs with same colours prevents lost items intended for incorrect client
Short tube to catheter preventing kinking and recurrent blockages
Packs of two for short term and packs of six for long term catheter usage
Multi design and same coloured pants for identification
Minimising or avoiding health complications eg; UTI's urinary tract infections
Bladder can be flush or adjacent to the skin for comfort due to connected fitting and balloon port
Velcro secures bladder into position internally for stability
Front flap also absorbs urine for additional storage
Litmus dye indicates when bladder needs replacing (by changing colour)
Easy access for carers to check the litmus dye indicator
Bladder contains sodium polyacrylate that turns urine into gel and prevents leakage
Packs of ten or carton disposable bladders for replacements
Bladder inserts when pants are flat for easy installing
Volume capacity is 500 mls for petite person and 750 mls for a larger person
Bladder and internal compartment is clear to sight any possible blood in urine
Bladder may be weighed to determine urine output Referring now to FIG. 6, there is illustrated a garment in the form of a pair of short trousers 35 suitable for activities such as riding a bicycle. The short trousers 35 include first (right) and second (left) leg portions 37R, 37L wherein each leg portion comprises an envelope of material 3R, 3L that receives a respective urine bladder 5R, 5L. Each envelope 3R, 3L is comprised of an internal layer 3a and an external layer 3b with a respective bladder 5 therebetween as shown in FIG. 7. By distributing the bladders evenly, one to each leg, the garment 35 provides a general weight equilibrium with balance and comfort. The volume capacity for each bladder is preferably 500 mls for petite persons and 750 mls for larger people. The bladders 5 wrap about 270 degrees around the front, outside and rear of each leg leaving the inner legs unencumbered to avoid chafing Preferably the legs of the short trousers are formed with inner loops 39 which retain catheter tubes 41 for connection to catheter ports in the form of connectors 26c (illustrated in FIGS. 10-16 in a non-swiveling form and in FIGS. 48-54 in a swiveling form). The connectors 26c are coupled to manifolds 6 each of the bladders 5R, 5L. The loops assist in preventing the catheter tubes 41 from kinking and causing skin irritation. The catheter tubes join in a "Y" junction connector 54, shown in cross section in FIG. 8, to a final tube that is coupled to the user. The "Y" junction connector 54 has an internal divider 55 to encourage even flow to both bladders.

Figure 6A:
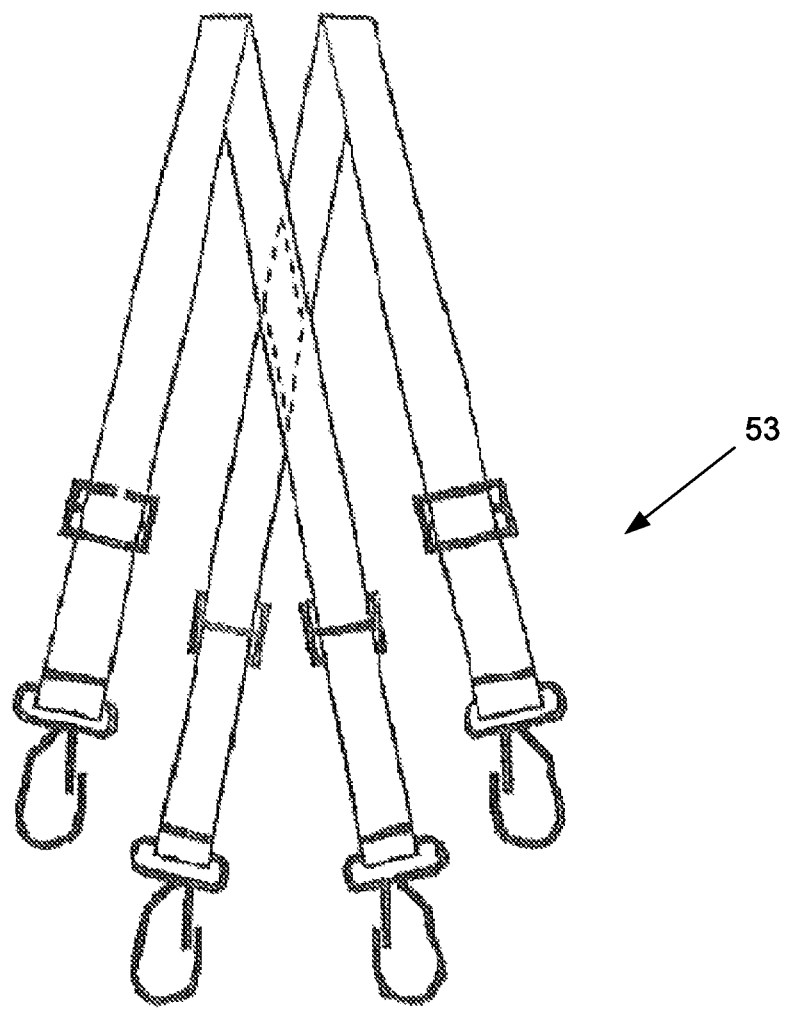
FIG. 6A depicts a pair of suspenders for use with the short trousers of FIG. 6.

In a preferred embodiment of the invention the short trousers 35 have a waist 49 that is formed with holes or loops 51 and so is adapted for suspenders 53 (FIG. 6A) to be fitted thereto to assist the user in holding up the weight of the bladders 5R, 5L.

Figure 9:
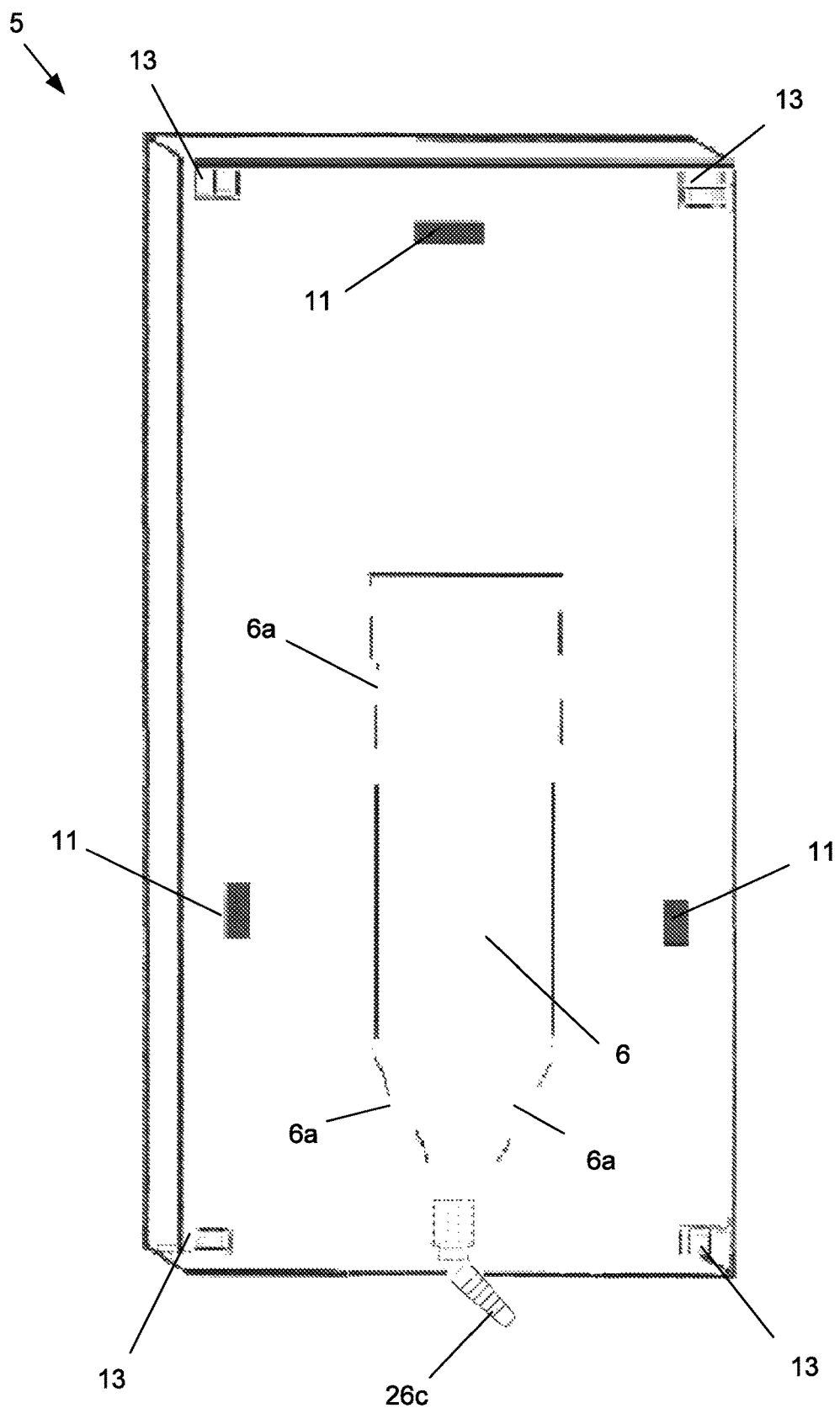
FIG. 9 further illustrates a leg bladder of the garment.
Figure 17:
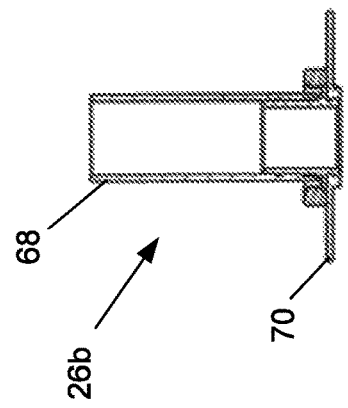
FIGS. 17 to 21 are various views of a bladder connector as used in the pants of FIG. 3A shown connected to a catheter tube.
Figure 18:
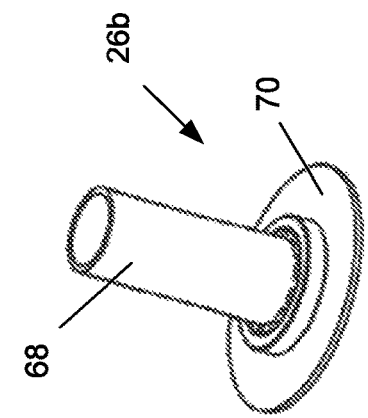
Figure 19:
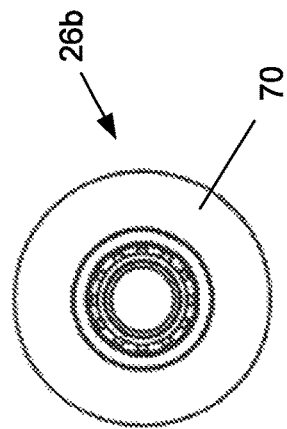
Figure 20:
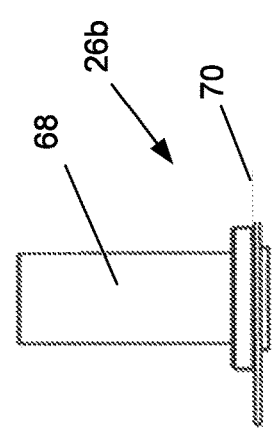
Figure 21:
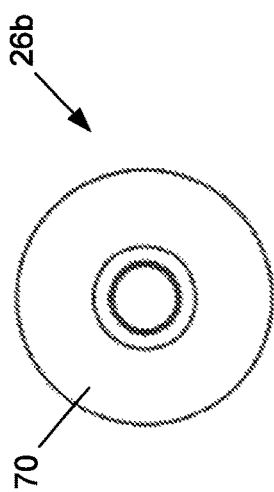
Figures 51, 52:
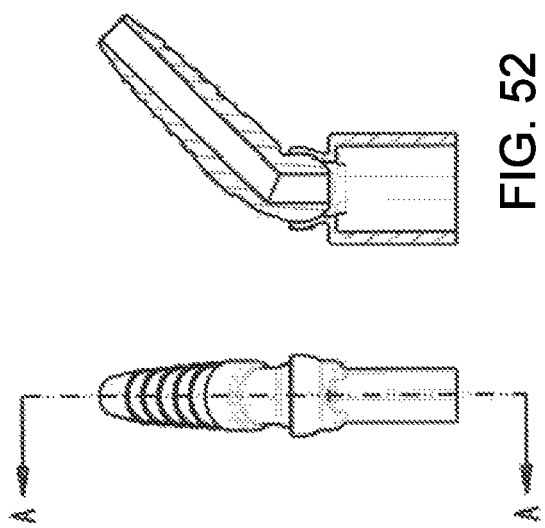
Figure 54:
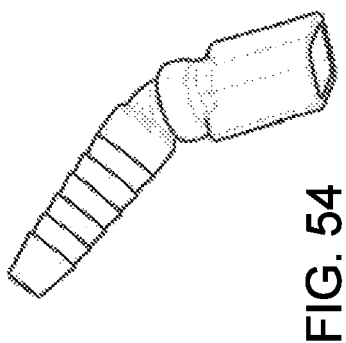
Figure 48:
Figure 50:
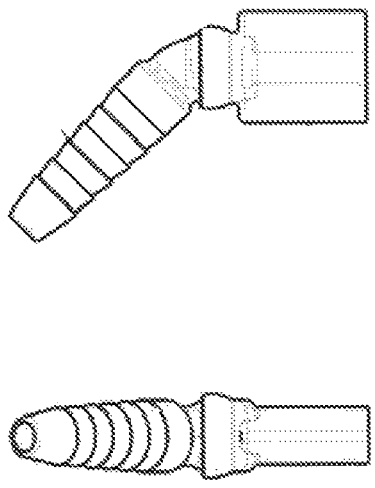
Figure 53:
Figure 49:

As shown in FIG. 9, the bladders 5R, 5L (generally referred to as item "5" in FIG. 9) are fitted with litmus dye indicator regions 11. Each bladder 5R, 5L is filled with sodium polyacrylate which surrounds an internal manifold 6 that is coupled to tube connector 26c for receiving a catheter tube. Preferably the short trousers 35 are made with lycra which is comfortable to wear and which reduces the likelihood of leaks.

The embodiment of the invention that has been discussed with reference to FIGS. 6 to 9 is intended for use in community activities, home environments and hospital rehabilitation. It is appropriate for nursing homes, hostels, youth and disability housing The embodiment of the invention that has been discussed with reference to FIGS. 6 to 9 is believed to have a number of benefits as follows:

Solving clients objectives eg; dignity, fashion style and accompanying all ages

No drainage bag attached to one leg/bed rails or dragging on the floor

Lycra short trousers bonds to skin for comfortable wearing with no leakage

Suspender belt is an additional option for fashion and immovable purposes

Internal loops supports catheter tube from kinking and skin irritation

Ideal for all activities eg; bike riding, surfing etc

Both short trousers legs have an internal pouch for bladder

Multi designs for fashion and same coloured pants for identification

Packs of two for short term and pack of six for long term catheter usage

Short trousers are washable and reusable for both males and females

Different packs with same colours prevents lost items intended for incorrect client Short tube to catheter preventing kinking and recurrent blockages Minimising or avoiding health complications eg; UTI's urinary tract infections Catheter tube has a "Y" fitting above fabric seam that leads to two bladders evenly on both legs One bladder on each leg for general equilibrium, balance and comfort Bladders are not flush or adjacent to the skin and connects flat Volume capacity for each bladder is 500 mls for petite person and 750 mls for larger person Velcro attaches the two bladders to two pouches internally for stability Bladders only wrap 270 degrees on both legs to prevent chafing Litmus dye indicates when bladders needs replacing by changing colour Pillow slip external openings for the bladders is absent from clients sight Bladder contains sodium polyacrylate that turns urine into gel and prevents leakage Easy access for carers to check the litmus dye indicator Urine output is tested by means of weighing bladder Bladder and internal compartment is clear to sight any possible blood in urine Packs of ten or carton disposable bladders for replacements Suspender belt prevents client constantly releasing Suspender belt is optional to cross at front for individual clients if necessary Prevents additional risk of the client/carer pulling out the catheter by supporting upwards In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

invention is not limited to specific features shown or described since the means herein described herein comprises preferred forms of putting the invention into effect. The invention is, therefore, claimed in any of its forms or modifications within the proper scope of the appended claims appropriately interpreted by those skilled in the art.

What is claimed is:

1. An incontinence assist appliance for a user comprising:
an envelope including a surface for contact with the user; and
a bladder that is removably receivable within the envelope, the bladder including a port for attachment of a catheter;
wherein the bladder contains a urine absorbing substance and provides a manifold for receiving urine from the port, the manifold being a hollow compartment contained internally within and surrounded on all exposed sides by the urine absorbing substance at a generally central region of the bladder and formed with a number of exit holes around a perimeter of the hollow compartment in the exposed sides of the hollow compartment, directed in different directions, for distributing urine to the urine absorbing substance.

2. An appliance according to claim 1, wherein the manifold comprises a plastic sack.

3. An appliance according to claim 1, wherein the urine absorbing substance comprises sodium polyacrylate.

4. An appliance according to claim 1, wherein the envelope is formed with one or more openings for the passage of the catheter from the bladder to the user.

5. An appliance according to claim 1, wherein the bladder includes a bladder status indicator, located outside the manifold, which indicates when the bladder is full and needs to be changed.

6. An appliance according to claim 5, wherein the bladder status indicator comprises a region of litmus dye.

7. An appliance according to claim 1, wherein the bladder has a perimeter shaped to correspond to the envelope.

8. An appliance according to claim 1, wherein the envelope includes an opening through which the bladder passes into an interior of the envelope for locating within the interior of the envelope in use.

9. An appliance according to claim 8, wherein a bladder status indicator is positioned on the bladder to locate adjacent the opening for ready inspection by a carer.

10. An appliance according to claim 1, wherein the port comprises a tubular connector for attachment of the catheter thereto.

11. An appliance according to claim 1, wherein the exterior of the bladder and the interior of the envelope are provided with complementary hook and loop regions for detachably holding the bladder fast within the interior of the envelope.

12. An appliance according to claim 1, wherein an outer topside of the envelope bears a cushioning layer.

13. An appliance according to claim 1, wherein the envelope in combination with the bladder presents as a cushion for seating of the user thereon.

14. An appliance according to claim 1, wherein the envelope comprises part or all of a wearable garment.

15. An appliance according to claim 14, wherein the envelope is formed with lateral wings for placement around opposed sides of a waist of the user and a medially extending flap for bringing up between the user's legs wherein outer edges of the lateral wings fasten to a front portion attached to the medially extending flap in use.

16. An appliance according to claim 15, wherein the envelope further includes a security flap that extends around the front portion for fastening to a rearward portion of the envelope in use that is remote to the user wearing the appliance to thereby make it difficult for the user to remove the envelope.

17. An appliance according to claim 15, wherein the envelope includes at least one strap which extends from one of the lateral wings across the front portion to the opposed lateral wings.

18. An appliance according to claim 15, wherein the front portion is formed with loops for passage of one or more straps therethrough.

19. An appliance according to claim 15, wherein the medially extending flap has a distal end that is formed with an opening for facilitating installation of the bladder.

20. A pair of short trousers including first and second leg portions each comprising an incontinence assist appliance according to claim 1.

21. A pair of short trousers according to claim 20, formed with inner leg loops which contain catheter tubes for connection to the bladders of the incontinence assist appliances.

22. A pair of short trousers according to claim 20, having a waist that is adapted for suspenders to be fitted thereto.

23. An appliance according to claim 1, further including a pressure care layer.

24. An appliance according to claim 23, wherein the pressure care layer comprises a cushioning layer that locates above the envelope that contains the bladder.

25. An appliance according to claim 24, wherein the cushioning layer comprises a polymer gel.

26. An appliance according to claim 1 further including a detachable cover.

\* \* \* \* \*